United States Patent [19]
Dreher et al.

[11] Patent Number: 5,303,709
[45] Date of Patent: Apr. 19, 1994

[54] RETINAL EYE DISEASE DIAGNOSTIC SYSTEM

[76] Inventors: Andreas W. Dreher, P.O. Box 22858, San Diego, Calif. 92192; Klaus Reiter, Ploeck II, W-6900 Heidelberg, Fed. Rep. of Germany

[21] Appl. No.: 808,479

[22] Filed: Dec. 16, 1991

[51] Int. Cl.$^5$ .................. A61B 6/00; A61B 13/00; A61B 5/103; A61B 3/14
[52] U.S. Cl. .................. 128/665; 128/745; 128/774; 351/206; 351/221
[58] Field of Search ............ 351/205, 206, 214, 221; 128/665, 645, 395, 630

[56] References Cited

U.S. PATENT DOCUMENTS

| | | | |
|---|---|---|---|
| 4,711,540 | 12/1987 | Yoshino | 128/633 X |
| 4,771,792 | 9/1988 | Seale | 128/774 |
| 4,883,061 | 11/1989 | Zeimer | 128/745 X |
| 5,029,220 | 7/1991 | Juday | 128/772 X |
| 5,098,426 | 3/1992 | Sklar et al. | 128/395 X |
| 5,148,807 | 9/1992 | Hsu | 128/649 X |
| 5,152,295 | 10/1992 | Kobayashi et al. | 128/665 |

Primary Examiner—David Isabella
Assistant Examiner—Elizabeth M. Burke
Attorney, Agent, or Firm—Ralph S. Branscomb

[57] ABSTRACT

Means and Method are provided for determining both the topography and the thickness of the nerve fiber layer at the fundus of the eye by measuring the polarization shift of the reflected probing light. The technique is greatly enhanced in the accuracy of its results by the utilization of a corneal polarization compensator, which lies at the heart of the invention.

24 Claims, 4 Drawing Sheets

RETINAL EYE DISEASE DIAGNOSTIC SYSTEM

BACKGROUND OF THE INVENTION

1. Field of Invention

This invention relates to a method and apparatus for assessing the thickness and topography of the retinal nerve fiber layer by measuring the polarization effect of the retina on an impinging light beam while simultaneously eliminating the polarization effects of the anterior segment of the eye on the same beam.

2. Description of the Prior Art

The retinal nerve fiber layer is the innermost layer of the human retina and consists of the ganglion cell axons which transmit the visual signal generated by the photoreceptors. The ganglion cell axons (nerve fibers) converge to the optic papilla where the optic nerve is formed that transmits the bundled visual information from the eye to the brain. In glaucoma and certain other diseases, there is damage to these nerve fibers which results in a loss of vision or even blindness. In order to detect glaucoma and to prevent further loss of vision, it is important to assess the exact condition of the retinal nerve fiber layer. One method for making this assessment that is in widespread use is that of employing a fundus camera with red-free illumination to photograph the retinal nerve fiber layer. Blue light (red-free) enhances the visibility of the transparent nerve fibers, and retinal locations with a nerve fiber layer defect appear darker than normal. However, no quantitative measurements can be obtained.

More recently, several methods have been developed that attempt to quantify the three-dimensional size and shape of the optic papilla which can be considered a bulk representation of the retinal nerve fibers. By analyzing the topography of the optic papilla and the surrounding retina, an indirect measure of the condition of the retinal nerve fiber layer can be obtained.

One of the current methods is stereoscopic fundus photography where two photographs of the fundus are obtained under different angles, and the depth or topography information is extracted by triangulation (see, for example U.S. Pat. No. 4,715,703).

Another method consists of projecting a stripe or grid pattern onto the fundus, which is observed under a certain angle. An algorithm calculates the apparent deformation of the projected stripes into the topography of the illuminated fundus region (see, for example, U.S. Pat. No. 4,423,931). More recent methods utilize the technique of confocal scanning laser ophthalmoscopy where a laser beam is scanned across the eye fundus in two dimensions in order to obtain real time video images on a TV monitor. By focusing the scanning laser beam on different layers of the retina and confocally detecting the light reflected from the fundus, optical section images of the retina can be obtained. These tomographic section images are analyzed to obtain the topography of the fundus. One apparatus (U.S. Pat. No. 4,900,144) employs a detection system consisting of two confocal detectors to obtain real-time topographic data from the scanning laser beam.

All of these techniques depend on the intensity of light reflected from the retinal surface as the sole probing tool for ascertaining the fundus topography. They are based on the assumption that the point of brightest reflection is at the internal limiting membrane, the interface between the vitreous and the retina. The point of maximum reflection is, therefore, assumed to represent the anterior surface of the nerve fiber layer. In reality, the light detected from the fundus is a mixture of light reflected from the internal limiting membrane and of light scattered from many points within the retina. Therefore, the maximum of the total intensity distribution of all light detected from the retina does not coincide with the most anterior surface of the retina, and a false topographic reading is presented by the conventional methods. Another major limitation of the conventional methods is the inability to measure thickness of the retinal nerve fiber layer. Whereas the topography of the fundus is a reasonable indicator of the thickness of the layer, it is indirect and suggestive only. A method of directly measuring the actual thickness of the retinal nerve fiber layer would represent a clearly valuable addition to the diagnostic tools available to the medical diagnostician.

It has been known [see for example, Journal of the Optical Society of America A 2, 72-75 (1985)] that the human retina has certain polarization properties. The instant inventors, in a paper delivered in 1991, [Technical Digest on Noninvasive Assessment of the Visual System, 1991 (Optical Society of America, Washington, D.C., 1991), Vol. 1, pp. 154-157], showed that the retinal nerve fiber layer was responsible for the polarization effect of the retina. The retinal nerve fiber layer consists of parallel axons which are form birefringent and change the state of polarization of light double-passing through it. The thicker the nerve fiber layer, the greater the alteration of the state of polarization of impinging light and thus the polarization of reflected light, yielding an opportunity to measure the thickness of the nerve fiber layer by gaging the relative shifting in polarization between the incident and reflected light at various points along the retinal nerve fiber layer.

The use of polarization measurements for mapping the retinal nerve fiber layer thickness, however, suffered from another potential limitation, which is, that the cornea and the crystalline lens of the eye also have birefringent qualities and therefore will alter the state of polarization of light double-passing it as well as the retinal nerve fiber layer, so that the total polarization shift of double-passing light is the sum of the shift caused by both the nerve fiber layer and the anterior segment of the eye. Without compensating for the polarization effects of the anterior segment, the measurement of the retinal polarization effect as a diagnostic technique would be of limited value.

SUMMARY OF THE INVENTION

The object of the present invention is therefore to provide a method and apparatus for measuring polarization effects of the retina while compensating for the polarization effects of the anterior segment of the eye in an automatic fashion. By compensating for the polarization effect of the anterior segment of the eye, all nerve fiber layer testing would yield meaningful results as a result of having the anterior segment polarization effects substantially neutralized. Furthermore, by neutralizing the polarization effects of the anterior segment of the eye and by the use of polarization-sensitive detection means, the light that has been reflected specularly from the internal limiting membrane at the anterior surface of the nerve fiber layer can be distinguished from the light originating from deeper retinal layers, therefore improving conventional topographic methods.

To attain this object, systems are provided for utilizing polarization probes for diagnosing the ocular fundus using a corneal polarization compensator for neutralizing the polarization effects of the anterior segment of the eye. The corneal polarization compensator comprises of a variable retarder through which monochromatic polarized laser light is passed and focused through the cornea onto either the posterior or anterior surface of the lens of the eye. The reflected light double-passes the anterior segment of the eye, travels back through the variable retarder and is confocally detected. The light is photoelectrically converted, and the signal is processed to control the retardation of the variable retarder in a closed feedback mode. The optical path in the compensation scheme is such that when the variable retarder is adjusted to the point where it neutralizes the polarization distortion of the cornea and lens, the signal at the photodetector is at its maximum and the variable retarder is fixed at this setting.

BRIEF DESCRIPTION OF THE DRAWINGS

FIG. 1 is a diagrammatic section taken through line 1—1 of FIG. 1a;

DETAILED DESCRIPTION OF THE PREFERRED EMBODIMENT

Figure 1:
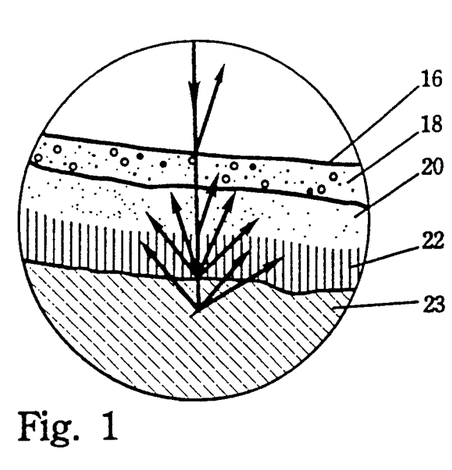
Figure 1A:
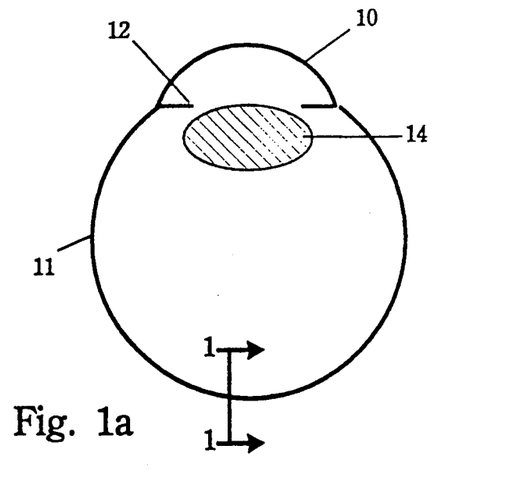
FIG. 1a is a diagrammatic view of the eye identifying parts of the anterior segment.

FIGS. 1a and 1 illustrates the eye 11, in which the cornea 10 serves as the foremost, transparent portion of the eye, behind which is the iris 12 and the lens 14. The interior of the eye 11 is of course filled with vitreous and at the rear of the eye is what is generally termed the retina composed of the layers illustrated, in FIG. 1, including the internal limiting membrane 16, the nerve fiber layer 18, the receptor system 20, the retinal pigment epithelium 22, and the choroid 23. All eye structure forward of the membrane 16 is considered the anterior segment of the eye for purposes of this disclosure and claim definitions.

This invention concerns itself primarily with the cornea, the lens, and the nerve fiber layer 18. It is this nerve fiber layer's topographical and thickness measurements which are crucial to the diagnosis of certain diseases, principal among which is glaucoma.

As indicated above, the nerve fiber layer 18 has birefringent properties, which means, in general, that a polarized light ray incident on the surface of the birefringent medium with its optic axis parallel to the surface will split into two rays of different polarization propagating in the same direction but with different velocities. The difference in travelling velocity results in a phase shift between the two rays, called retardation, and has the effect of altering the polarization of the light. The thicker the birefringent medium, the larger is the retardation of light passing through the medium. A so-called "quarter wave" retarder incorporates a birefringent medium that retards one of the rays that is split out of incident light 90 degrees relative to the other, and thus will convert linear polarization to circular polarization, and vice-versa.

The nerve fiber layer 18 has the property of birefringence. The cornea and the lens also have birefringent properties, although the birefringence of the lens is small compared to the cornea. There are no other known birefringent layers in the eye. The eye polarization characteristics will be used to measure the thickness and the topography of the nerve fiber layer.

Figure 2:
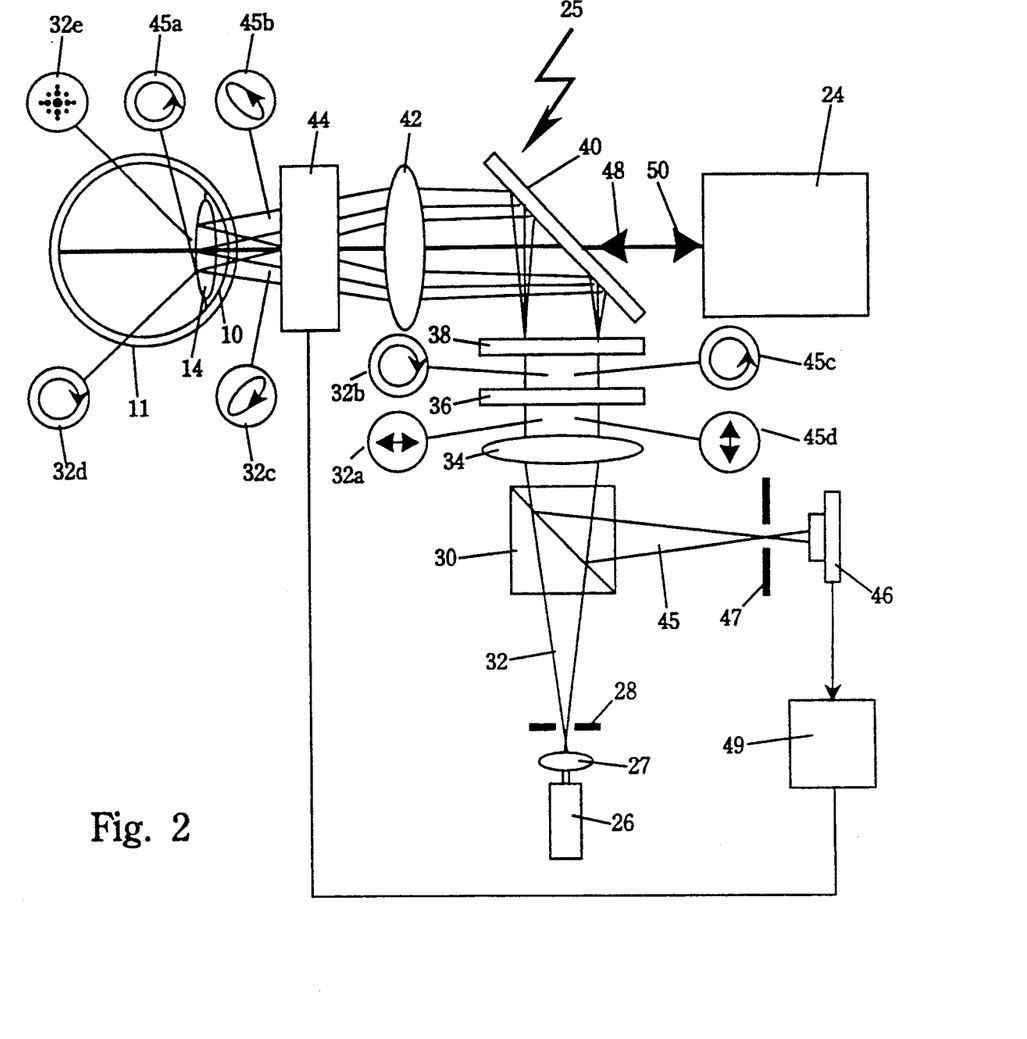
FIG. 2 illustrates diagrammatically the main parts of a embodiment of the corneal polarization compensator using an ellipsometer.

Turning now to FIG. 2, a complete system for diagnosing the thickness of the nerve fiber layer is diagrammatically shown. All of the structure in FIG. 2 except for the ellipsometer 24 are for the purpose of compensating for the polarization shifting caused by the cornea and lens. (In this disclosure, polarization "shifting" is the term used generically to cover all types of polarization changes, including rotation of the optical axis of polarized light, the change of linear to elliptical or circularly polarized light or vice-versa, and any combination of these). The term "corneal polarization compensator" is used for describing the device for compensating for the polarization effect of the anterior segment of the eye.

The ellipsometer 24 is for the purpose of accurately measuring the polarization shift of a beam of light which double-passes the nerve fiber layer. This shift correlates to the thickness of the nerve fiber layer once the corneal polarization compensation has been effected.

The corneal polarization compensator 25 utilizes a laser diode 26 which provides a beam of light that is focused by a lens 27 onto the pinhole 28 and expands as a cone until it impinges upon the polarizing beamsplitter 30. This beamsplitter has two purposes, the first of which is to polarize the incident compensation beam 32, which it does as is indicated by the legend indicated at 32a, illustrating the linear transverse polarization that the beam has at this point. The beam subsequently passes through a collimating lens 34 and a quarter wave retarder 36, which converts the beam 32 from linear polarization illustrated in the legend 32a to the clockwise circular polarization indicated in the legend 32b.

At this point, the incident compensation beam 32 passes through a reticulated or rectangular diffraction grating 38, which has the effect of corpuscularizing the light into a plurality of beams, so that a plurality of focus points as indicated at 32(e) are used by the compensator rather than a single spot. The beam is reflected on the beamsplitter 40, converged by the converging lens 42, and passed through the variable retarder 44, which in the preferred embodiment is a liquid crystal retarder. This retarder changes the polarization of the incident beams from circular polarization to elliptical as illustrated at 32c, still being clockwise in sense.

At this point, the plurality of converging sub-beams of the whole beam 32 from the variable retarder 44 converge, passing through the cornea 10 and lens 14, becoming circularly polarized as indicated at 32d and reflecting as return compensation beam 45 from the posterior surface of the eye lens 14, as illustrated. This reflected or return compensation beam is polarization shifted by the double-passage through the cornea and lens not only to circular polarization as indicated at 32d, but is shifted to reverse the direction of the circular polarization as a result of the reflection, as indicated at 45a. (For purposes of the claims, the incident and return beams are each treated singularly, but each includes all of the composite beams split out by the diffraction grating and then re-converged.)

The return compensation beam 45 has polarization transversely illustrated in the legends 45a–45d, above and to the right of the configuration. Immediately upon reflecting from the lens surface, the right-hand circular polarization is changed to left-hand circular polarization 45a, and shifts to elliptical polarization as indicated at 45b upon passage through the cornea 10 and lens 14. The return compensation beam 45 passes through the variable retarder 44 where its polarization is restored to circular polarization as indicated in 45c, and travels back through the elements that the impinging beam went through, passing through a polarization shift at 45d until the beam arrives at the polarizing beamsplitter 30.

It will be remembered that when the beam initially passed up through this beamsplitter, it was transversely polarized as indicated at 32a. It is a property of a polarizing beamsplitter to transmit light that is polarized perpendicularly to its reflecting surface, and to reflect light that is polarized parallel to its reflecting surface. As the return compensation beam is now completely linearly polarized, parallel to the reflecting surface of the beamsplitter 30, the return compensation beam 45 is reflected to the right, towards the photodetector 46. The return compensation beam is focused by the lens 34 onto the pinhole 47 in front of the photodetector 46. The pinholes 47 and 28 are located in optically conjugate planes to the focal points formed at the posterior surface of the lens. This confocal arrangement assures that stray light reflected from other areas than the focal points is blocked by the pinhole 47 and cannot reach the photodetector 46.

In other words, when all light of the return beam 45 impinging downward upon the polarizing beamsplitter 30 is linearly polarized orthogonally to the direction of the upwardly travelling beam 32, all of the light reflected from the surface of the lens 14 would travel through to the photodetector 46. Thus, with no polarization shift at all caused by the anterior segment of the eye, incident and return compensation beams 32 and 45 would have the polarization states shown at 32a and 45d, respectively. The variable retarder is adjusted to maximize the intensity of light in the polarized state shown at 45d as closely as possible.

The photodetector 46 transforms the intensity of impinging light into an electrical signal that is fed into the electronic feedback circuit 49. Because the cornea and lens shift the polarization, the variable retarder is varied by the electronic circuit 49 until the electric signal coming from the photodetector 46 is maximized. FIG. 2 illustrates states of polarization of incident and return beams after the compensator has already been adjusted to compensate for anterior segment polarization shift.

After the variable retarder 44 has been adjusted for the optimal compensation of corneal and lenticular polarization distortion, the ellipsometer 24 is free to pass its incident diagnostic beam 48 through the beamsplitter, having its beam polarization-compensated by the variable retarder (compensator) 44, and receive a return beam 50 that actually reflects not the polarization distortion caused by the cornea and lens, but only that of the nerve fiber layer in question. This polarization information is then captured and can be analyzed according to ellipsometry techniques that are known in the prior art or as set forth in this disclosure.

This process has been disclosed having the incident and return compensation and diagnostic beams double-passing the variable retarder 44. However, with a different geometrical arrangement, only one of the compensation beams and one of the diagnostic beams would have to pass through the variable retarder, and it could be either the incident beams or the return beams, or one of each. The simplest geometry and probably the most accurate results involve double-passing both beams through the variable retarder as shown, however.

The corneal polarization compensator 44 is used in all of the techniques that are discussed in this disclosure. It has already been stated that the ellipsometer can be used basically by itself, as shown in FIG. 2, along with scanning and analysis equipment, not shown in FIG. 2, to provide a reasonably accurate map of the thickness of the retinal nerve fiber layer. A computer frame 51 shown in FIGS. 3 and 4 illustrates the appearance of a typical nerve fiber layer thickness or topography map.

Figure 3:
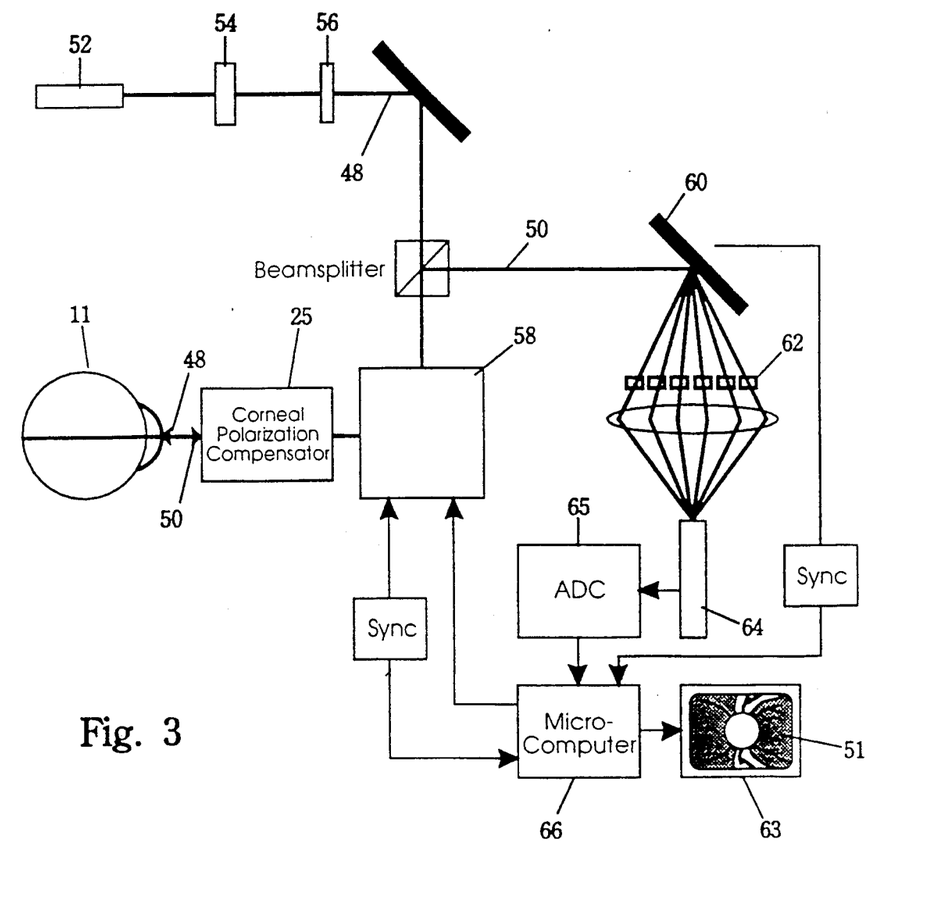
FIG. 3 illustrates diagrammatically one manner in which the nerve fiber layer thickness is mapped with the use of a sequence of polarizers of different states of polarization; and, FIG. 4 illustrates a topographical mapping system.
Figure 4:
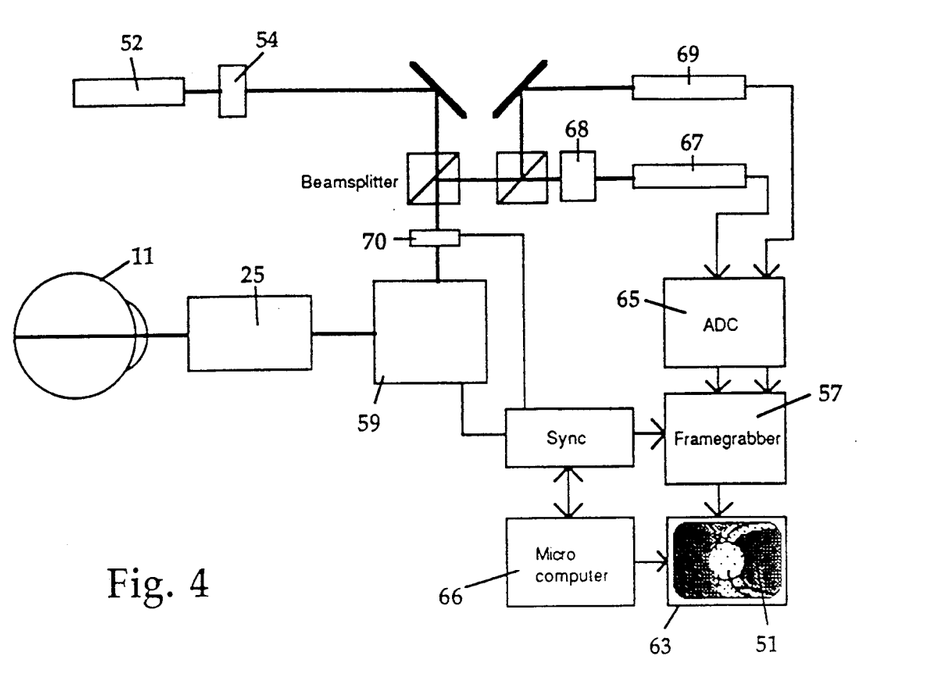

One way of measuring and mapping the thickness of the nerve fiber layer is shown in FIG. 3, with a system that uses an ellipsometer not described in the prior art. It has an incident diagnostic beam 48 produced by the laser 52, linearly polarized by linear polarizer 54, converted to circular polarization by quarter-wave retarder 56 and scanned across the ocular fundus by the scanning unit 58. At each point of the scan, the return diagnostic beam 50 is then again scanned by an oscillating mirror 60 sequentially across a plurality of polarizers 62 forming an array. Six polarizers are shown in the array of FIG. 3, and as the return beam reaches the detector 64 in sequence from each of the polarizers the beam intensity is photoelectrically converted by the detector 64 into an electrical signal that is digitized by an Analog-to-Digital Converter 65 and stored in the memory of the computer 66. From the data stored in the computer, the four elements of the Stokes vector of the incident diagnostic beam 48 are compared to the calculated Stokes vector of the return diagnostic beam, and the change in polarization at the current measuring location is displayed on the CRT display 63. Subsequently, the incident diagnostic beam is guided by the scanning unit 58 to the next measuring site.

The scanned polarizer system of FIG. 3 is very diagrammatic, and the polarizers could be either reflective or transparent and would ordinarily have a mirror system converging the respectively produced beams onto the detector. For every point scanned on the ocular fundus, all of the polarizers 62 would be scanned by the oscillating mirror 60.

It would be clear to a person skilled in the art that the principle described can also be performed by changing the time sequence of the polarization data measurement process. For example, instead of scanning a single point at 58 while mirror 60 undergoes a complete scanning cycle, the incident diagnostic beam 48 could first be scanned by the scanning unit 58 over the whole examination area, while the return diagnostic beam 50 passes only one of the polarizers. In the next step, the procedure is repeated, but the return diagnostic beam 50 is passed through the second polarizer, and so on, scanning a complete frame for each of the polarizers 62 before moving on to the subsequent polarizer.

Furthermore, the process of imaging the examination area by a scanning laser beam could be replaced with illuminating the fundus with an extended light source and replacing the detector 64 with a camera.

Thus far, the specification has been discussing not topography but rather the gaging of the thickness of the nerve fiber layer and the creation of, in essence, a thickness map display. It is also possible using a very similar technique to create a topographical map which is considerably more accurate than the usual confocal-produced topographical maps that currently are made using light intensity only, not polarization shifting.

FIG. 4 is a diagrammatic illustration of a system similar to FIG. 3 which will produce a topographical map of the retinal nerve fiber layer. The scanning unit 58 is replaced by a three-dimensional scanning unit 59, and the detector 64 is replaced by a confocal detection unit 67. It is similar to the typical confocal system that is now used, except that the optical data that is received back from the nerve fiber layer is sorted by discarding any data, that is any light rays, that are returning from the eye having altered polarization. The polarization of the incident beam is known and can be compared with the analyzer 68 to the polarization of the return beam.

Figure 7:
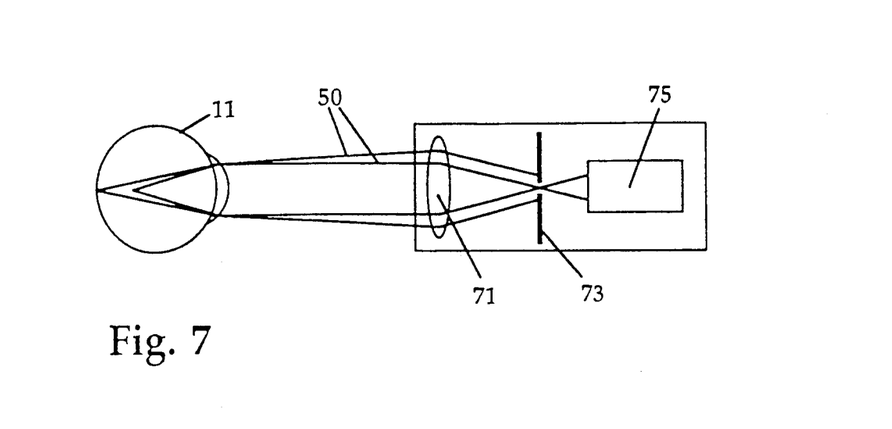

Any of the detectors, indicated at 64, 67 or 69, could be configured for confocal detection to eliminate light not returning from the selected focal plane in the eye by incorporating a lens 71 and a pinhole diaphragm 73 before the actual detector structure itself 75 as indicated in FIG. 7.

Because the corneal polarization compensator eliminates polarization shifting caused by the anterior segment of the eye, and the polarization of the incident light beam is known, any return light which is changed in its state of polarization is known to have been reflected from a surface deeper than the nerve fiber layer surface 16 inasmuch as there would not be a polarization shift were the reflection to take place only from the surface. Thus, the typical confocal topographical mapping technique can be enhanced by discarding all light information in which the light rays have been altered in their polarization state.

The amount of information that can be gleaned from the interior of the eye utilizing these techniques incorporating the cornea polarization compensator could be quite great. For example, topographical maps of deeper layers of the eye than the surface of the nerve fiber layer can be made by rejecting the light in the polarization state of the initial beam, rather than vice-versa. This could possibly produce a topographical map of a surface posterior to the nerve fiber layer. That is, light reflected from a surface more posterior than the nerve fiber layer would have a different polarization than the incident light, and thus it would be recorded and mapped rather than the non-adulterated incident ray that would be used to produce topographical map of the anterior surface of the nerve fiber layer.

The last method of measuring nerve fiber layer thickness to be discussed herein uses the same basic equipment shown in FIG. 4 for topography mapping, except that a polarization rotator 70 is interposed in the light path of the incident or return diagnostic beam, or both the incident and the return diagnostic beams, and a second detector 69 measures the absolute intensity of the return diagnostic beam, independent of the polarization state of that beam. Understanding this technique depends on understanding basic retinal anatomy illustrated in FIGS. 5 and 6. The retinal nerve fiber layer 14 comprises an array of radially arranged nerve fibers 72 which converge to form the optic papilla 74. The radially arranged nerve fibers are about half the diameter of the wavelength of visible light and at any one point simulate parallel fibers having directional birefringent properties.

Figure 5:
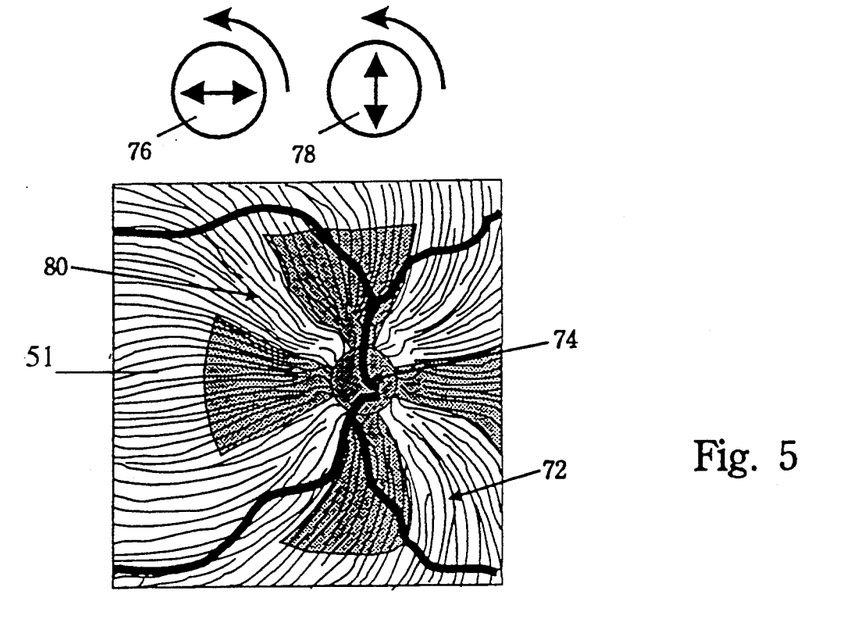
FIG. 5 illustrates the appearance of the retinal nerve layer under illumination with linearly polarized light and detection with a crossed polarizer, corneal birefringence being eliminated.
Figure 6:
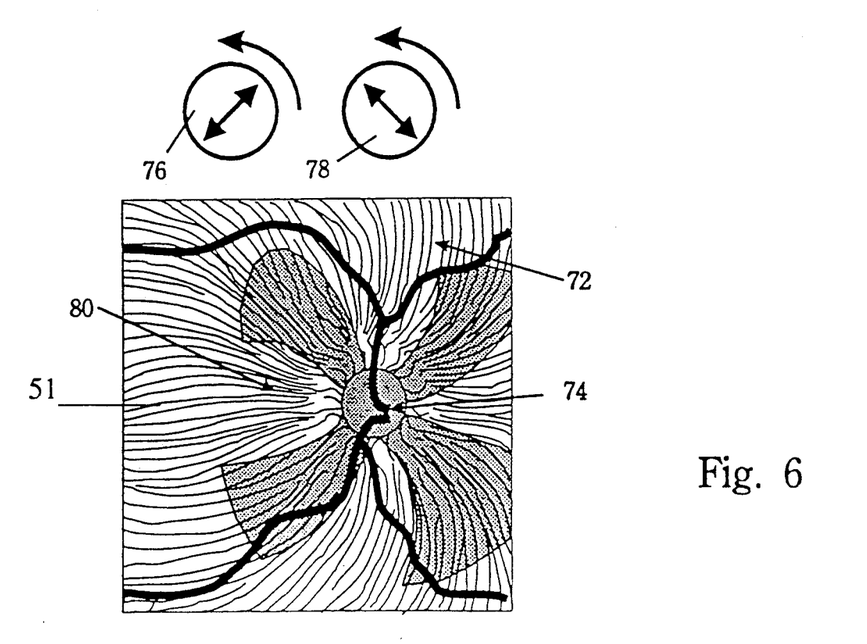
FIG. 6 is identical to FIG. 5, but illustrating measurement taking place with the orientation of the polarization axis of the illuminating beam and the detection filter both being rotated about 45 degrees; and, FIG. 7 is a diagrammatic illustration of a photodetector incorporating a focusing lens and a pinhole diaphragm for use in confocal detection techniques.

This radial array of nerve fibers acts as a linear birefringent medium due to the local parallelism and wavelength order-of-magnitude spacing of the fibers. It is illuminated with linearly polarized light, and the reflected from the ocular fundus is passed through an analyzer with an orthogonally polarized filter 68 to a photodetector or collector. The transverse polarizations of the incident beam and the filter are indicated respectively at 76 and 78. A "cross" pattern of brightness, indicated at 80, will appear at the detector. There will be darkness along the polarization axes of both the incident light beam and the analyzer filter. The bright arms correspond to areas of the nerve fiber layer having fiber orientation rotated 45 degrees to either side of the polarization axis of the incident beam (and the analyzer filter). The bright portions of the cross give an accurate indication of the thickness of the nerve fiber layer at these points, as substantial change in polarization caused by substantial nerve fiber layer thickness will shift the polarization of the light adequately to pass through the analyzer polarization filter.

In order to obtain a thickness analogue at every point of the nerve fiber layer, the polarization axes of the incident beam and analyzer filter are synchronously rotated through 90 degrees, with a brightness reading taken every 2 degrees or so, for every point on the fundus that will appear on the map. The brightest return beam the detector picks up for every scanned point on the fundus is cumulated with every other brightest point and formed into an intensity map that corresponds to the relative thickness of the nerve fiber layer point by point.

The second photodetector 69 is used to measure the total amount of reflected intensity of the return diagnostic beam at the corresponding points on the fundus. By normalizing the intensity values obtained with the first photodetector 67 with the corresponding intensity values obtained with detector 69, absolute changes in the state of polarization of the return diagnostic beam are calculated.

This technique produces a nerve fiber layer thickness map similar to that produced by the first two techniques using ellipsometers. It is an alternative technique.

All of the diagnostic techniques and equipment disclosed herein depend on the polarization characteristics of the ocular fundus in order to be feasible, and depend on the compensating capability of the corneal polarization compensator in order to produce useable results. The polarization diagnostic techniques disclosed herein make a substantial contribution to the ability to diagnose diseases of the interior of the eye, especially early diagnosis of glaucoma.

DEFINITIONS OF TERMS USED IN THE DESCRIPTION AND CLAIMS

ABSOLUTE INTENSITY refers to the sum of the intensities of all of the component parts of a light beam, including polarized and unpolarized segments.

ANALYZER, or POLARIZATION ANALYZER: a device whose output is a function of the polarization state of analyzed light in some way, and it may be no more than a polarization filter which attenuates light which is not linearly polarized with a specific orientation of the POLARIZATION AXIS or it may correlate the polarization state or shift with another quantity. An ANALYZER may or may not produce results which are directly readable by the operator.

ANTERIOR SEGMENT OF THE EYE refers to all parts of the eye forward of the OCULAR FUNDUS, in this instance those parts which pass light incoming through the cornea. It includes the vitreous, lens, aqueous, and cornea and any membranes.

BIREFRINGENCE is a POLARIZATION PROPERTY of certain materials which retards the propagation velocity of only part of a transmitted beam, causing it to have a phase lag with the rest of the beam, shifting the polarization phase; birefringence is not the only possible polarization property.

FUNDUS = ocular fundus

KNOWN STATE OF POLARIZATION refers to the POLARIZATION STATE that is controlled so interaction with equipment such as polarization filters produces meaningful and possibly measurable results. The phrase does not mean that the operators necessarily know exactly what the polarization state is at a given time.

MODULATION of the polarization state of light is the alteration of the polarization state over time analogous to frequency or amplitude modulation; the retardation can be modulated, which if executed through a complete 360° cycle causes the polarization to cycle through linear, elliptical, circular, elliptical, linear, reverse-direction elliptical, circular, elliptical and back to linear. Or, the polarization axis can be modulated by being rotated about the optical axis. Any alterable polarized condition in which the alteration is detectable could be modulated.

OCULAR FUNDUS: generically the layers of the eye posterior to the internal limiting membrane covering the anterior surface of the nerve fiber layer (primarily the retina and the sclera); the anterior surface of the internal limiting membrane separates the ANTERIOR SEGMENT and the FUNDUS, as the terms are used in this disclosure.

POLARIZATION AXIS. Light behaves as a transverse wave in which the waves vibrate perpendicularly to the direction of propagation. The polarization axis of light is oriented in the direction of vibration, orthogonal to the propagation direction.

POLARIZATION EFFECTS on light refers to alterations made to the polarization state of incident light by objects and media as a result of their POLARIZATION PROPERTIES;

POLARIZATION PROPERTIES refers to the characteristics of specific materials and structure relating to the POLARIZATION EFFECTS they have, or do not have, on the POLARIZATION STATE of incident light, such as polarizing unpolarized light, rotating the POLARIZATION AXIS, affecting the degree or type of polarization, or not affecting polarization at all.

REVERSAL OF SENSE OR DIRECTION of polarized light: light reverses, left-hand/right-hand, the polarization sense when it is reflected from a specular surface.

We claim:

1. For an eye having an anterior segment which includes a cornea, a lens, and a pupil, and a fundus posterior to the anterior segment which includes a retina and a retinal nerve fiber layer, a method for detecting eye diseases by examining polarization properties of the fundus while substantially compensating for polarization effects of the anterior segment of the eye, comprising the following steps:
    (a) illuminating the fundus including the retinal nerve fiber layer through the pupil and anterior segment including the cornea and lens, with at least partially polarized incident light in an incident diagnostic beam of a known polarization state;
    (b) detecting reflected light reflected from the fundus from the incident diagnostic beam as a return diagnostic beam having a state of polarization with a polarization-sensitive detection device; and
    (c) substantially compensating for the polarization effects of the anterior segment of the eye through which said diagnostic beams pass such that the state of polarization of said return diagnostic beam can be analyzed and compared to said known polarization state of the incident diagnostic beam to determine degree of alteration of the state of polarization of said return diagnostic beam due to a net polarization effect of the fundus, and determining said net polarization effect of the fundus from said degree of alteration from which an inference can be made regarding the presence and progress of certain eye diseases due to a net polarization effect of the fundus.

2. A method according to claim 1 wherein step (c) is accomplished by the use of a corneal polarization compensator.

3. A method according to claim 2 wherein said corneal polarization compensator is interposed in the propagation path of at least one of said beams.

4. A method according to claim 3 wherein said corneal polarization compensator includes a variable retarder, and step (c) comprises adjusting said variable retarder to achieve a known amount of combined net retardation induced in light passing through said variable retarder and the anterior segment of the eye.

5. A method according to claim 4 wherein step (c) is executed by adjusting said variable retarder such that the combined net retardation of said variable retarder and the anterior segment of the eye is substantially null such that retardation of the return diagnostic beam detected instep (b) indicates substantially as closely as possible retardation caused by the fundus independent from any retardation of the anterior segment of the eye.

6. A method according to claim 5 wherein step (c) is accomplished by focusing an incident compensation beam on a surface of the lens of the eye producing a reflected compensation beam, passing both of said compensation beams through said variable retarder and adjusting said variable retarder until the compensation beams on a side of the variable retarder remote from the eye are both in substantially identical states of polarization, except for a 180-degree phase shift caused by the reflection at the surface of the lens of the eye.

7. A method according to claim 6 wherein said incident compensation beam is laser-produced and linearly polarized with a first polarization axis and passed through a quarter-wave retarder, said reflected compensation beam returns through said quarter-wave retarder to become linearly polarized with a second polarization axis orthogonal to said first polarization axis absent the polarization effects of the anterior segment of the eye and variable retarder, and said variable retarder is adjusted so that the state of polarization of the reflected compensation beam after passing through the quarter-wave retarder as closely as possible resembles a state of linear polarization with a polarization axis orthogonal to said first polarization axis.

8. A method according to claim 1 wherein said polarization sensitive detection device of step (b) is an ellipsometer.

9. A method according to claim 8 and including the steps of scanning said incident diagnostic beam across said fundus to a plurality of geometric points of incidence and mapping the degree of alteration of the state of polarization of said return diagnostic beam as a function of said geometric points of incidence.

10. A method according to claims 8 or 9 wherein said incident diagnostic beam illuminates said fundus to generate a plurality of illuminated points, and at least one of said diagnostic beams is modulated in it state of polarization to produce a sequence of modulated polarization states, and for each such modulated polarization state of said diagnostic beams said return diagnostic beam is analyzed for each of said illuminated points of the fundus to derive a polarization indicator for each of said illuminated points, and the polarization indicators for all illuminated points of the fundus for each of said modulated polarization states are stored in a computer memory as modulated-polarization-state-specific images, and including the further step of calculating the degree of alteration of the state of polarization of said return diagnostic beam from the modulated-polarization-state-specific polarization images stored in the computer memory for each illuminated point of the fundus, and including the further step of mapping said degrees of alteration of the state of polarization of said return diagnostic beam as a function of the illuminated points of said fundus.

11. A method according to claim 1 wherein said polarization sensitive detection device comprises a detecting scanner which scans said return diagnostic beam sequentially through a plurality of polarizers of different polarization states and including the steps of sequentially intensity-analyzing said return diagnostic beam after it sequentially passes through each of said plurality of polarizers to produce a polarizer-specific intensity value for each of said polarizers from which the state of polarization of said return diagnostic beam can be calculated.

12. A method according to claim 11 and including a diagnostic scanner scanning the incident diagnostic beam sequentially across said fundus to a plurality of geometric points of incidence on said ocular fundus and including the step of mapping the degree of alteration of the state of polarization of said return diagnostic beam as a function of said geometric points of incidence scanned on said fundus.

13. A method according to claims 11 or 12 wherein said incident diagnostic beam illuminates said fundus to generate a plurality of illuminated points, and said return diagnostic beam from each illuminated point of said fundus is collected through one polarizer of said plurality of polarizers resulting in a polarizer-specific polarization image, and said polarizer-specific polarization image is stored in a computer memory, and including the step of repeating the procedures of illuminating said fundus, collecting said return diagnostic beam, and storing said polarizer-specific polarization image, for each polarizer of said plurality of polarizers, and including the further step of mapping the degree of alteration of the state of polarization of said return diagnostic beam for each image point of said polarization images stored in said computer memory.

14. A method according to claim 1 wherein said retinal nerve fiber layer exhibits birefringence and has an anterior surface and a posterior surface, and step (a) includes substantially focusing said incident light on a retinal layer generally posterior to said posterior surface of the nerve fiber layer, and step (b) comprises detecting the degree of alteration of the state of polarization of said return diagnostic beam caused by the birefringence of the retinal nerve fiber layer, and including the further step of transforming said degree of alteration of the state of polarization of said return diagnostic beam into a nerve fiber layer thickness reading and including the further step of displaying said nerve fiber layer thickness reading as an image correlating brightness with the thickness of said retinal nerve fiber layer to define a mapped nerve fiber layer thickness image.

15. A method according to claim 14 and including the step of scanning the incident diagnostic beam across said retinal nerve fiber layer and further including the step of mapping said nerve fiber layer thickness reading.

16. A method according to claim 1 wherein said retinal nerve fiber layer has an anterior surface and including the step of focally scanning said incident diagnostic beam across said anterior surface in at least one focal plane with a diagnostic scanner, and including the further step of creating a topographic map of said anterior surface by mapping confocally detected scanned points reflected from the anterior surface of said retinal nerve fiber layer displaying minimal retardation in the reflected light.

17. A method according to claim 1 wherein said incident diagnostic beam has a first polarization axis, and said return diagnostic beam has a second polarization axis, and step (a) includes rotating the polarization axis of at least one of said diagnostic beams to create a plurality of different polarization states of said diagnostic beams.

18. A method according to claim 17 and including the step of scanning said incident diagnostic beam across said fundus.

19. A method according to claim 17 or 18 wherein the polarization axis of at least one of said diagnostic beams is rotated through substantially 90° at every illuminated point of said fundus.

20. A method according to claim 19 and including the steps of analyzing said reflected light and producing an intensity map of the retinal nerve fiber layer which correlates a maximum level of retardation achieved throughout the 90° rotation of the polarization axis of at least one of said diagnostic beams at each illuminated point on the retinal nerve fiber layer with a corresponding light intensity level on said map.

21. A method according to claim 17 or 18 wherein the polarization axis of at least one of said diagnostic beams is rotated through at least 45° at every illuminated point of said fundus.

22. A method according to claim 21 wherein said fundus contains an optic papilla with a center and including the steps of analyzing said reflected light at fundus locations along at least one line passing through the center of the optic papilla under a fixed angular position with respect to the rotating polarization axis of one of said diagnostic beams.

23. A method according to claim 22 wherein said return diagnostic beam has an absolute intensity and including the step of detecting said absolute intensity of said return diagnostic beam at each point scanned on the fundus.

24. A method according to claim 1 and including the step of displaying an image of the fundus in which brightness of each image point represents deviation of the state of polarization of the reflected light from the incident light for each point of illumination of the fundus.

* * * * *